United States Patent [19]
Griebel

[11] Patent Number: 4,993,071
[45] Date of Patent: Feb. 12, 1991

[54] POST-LARYNGECTOMY SPEECH AID

[75] Inventor: Peter Griebel, Freiburg, Fed. Rep. of Germany

[73] Assignee: Dr. Kuhn & Co. GmbH, Cologne, Fed. Rep. of Germany

[21] Appl. No.: 255,703

[22] Filed: Oct. 11, 1988

Related U.S. Application Data

[63] Continuation of Ser. No. 897,011, Aug. 15, 1986, abandoned.

[30] Foreign Application Priority Data

Aug. 17, 1985 [DE] Fed. Rep. of Germany ....... 3529553

[51] Int. Cl.$^5$ ............................................ H04R 25/00
[52] U.S. Cl. .................................................... 381/70
[58] Field of Search ............. 381/70, 103; 84/DIG. 9, 84/ 711, 665, 671, 647

[56] References Cited

U.S. PATENT DOCUMENTS

| | | | |
|---|---|---|---|
| 3,732,370 | 5/1973 | Sacks | 381/103 |
| 3,775,545 | 11/1973 | Tsukamoto et al. | 84/697 |
| 3,914,550 | 10/1975 | Cardwell, Jr. | 381/70 |
| 4,039,756 | 8/1977 | Burtschi | 381/70 |
| 4,550,427 | 10/1985 | Katz et al. | 381/70 |
| 4,677,890 | 7/1987 | Yannes | 84/1.19 |

Primary Examiner—Forester W. Isen
Attorney, Agent, or Firm—Felfe & Lynch

[57] ABSTRACT

A speech aid for laryngectomy patients is described and comprises an electromechanical transformer with a power output stage connected upstream, a pulse generator for the production of a basic frequency, manually operated switches and electrical filters designed to vary the pulse frequency as a function of time. The power output stage in this respect comprises an electronic switch which is controlled by the basic frequency and a controlling pulse generator which switches the electronic switch off at least with temporal priority over the basic frequency.

7 Claims, 4 Drawing Sheets

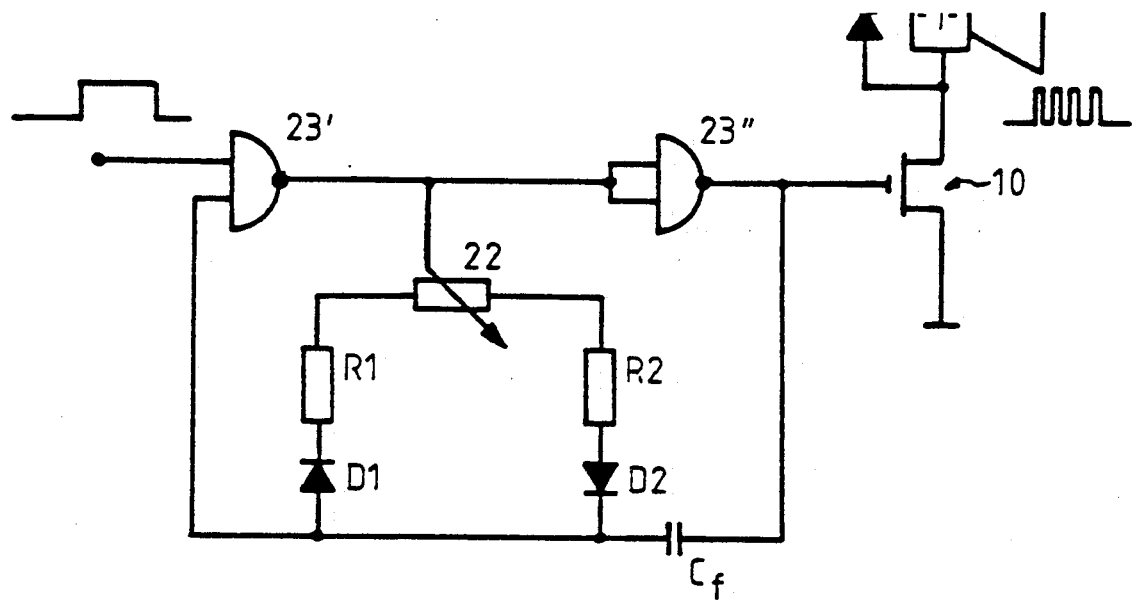
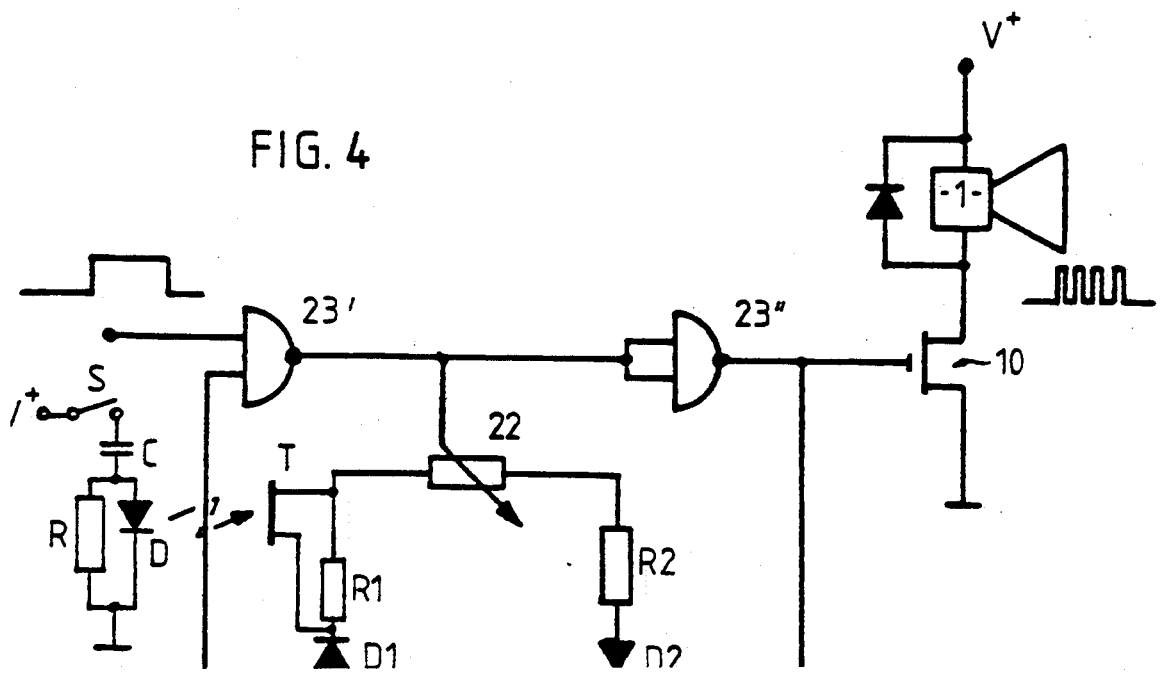
FIG. 4

POST-LARYNGECTOMY SPEECH AID

This is a continuation of application Ser. No. 897,011, filed Aug. 15, 1986, now abandoned.

The invention relates to a post-laryngectomy speech aid.

BACKGROUND OF THE INVENTION

Speech aids for use by persons who have had laryngectomies electrically produce mechanical vibrations which are applied externally, passed through the soft tissues of the neck into the area of the mouth and throat and modulated by means of tongue and throat movements into comprehensible speech. Speech aids of this type, in most cases, have the shape of torch-shaped flashlights to be held in the hand by their shaft-like handles and pressed against the neck at their, flared ends, which contain the electromechanical vibration transducers. Rechargeable batteries are in most cases used as a source of power.

A drawback of such speech aids has been either that very large batteries have to be used, making long-term use of the device tiring, or that the batteries must be frequently recharged so, that a spare device must be available.

In addition, if speech which is suitably articulated for ready comprehension is to be produced, the fluctuations in loudness and intonation of normal voice production must be matched. These fluctuations vary widely, so that a large number of loudness and tone parameters must be produced. At least some of this has had to be carried out manually by the user.

This makes learning how to handle the speech aid more difficult and also increases its size and heaviness as a result of the multiplicity of components required.

SUMMARY OF THE INVENTION

Starting from the above-mentioned prior art, an object of the present invention is, therefore, to provide a speech aid of as low a cost and as small a size as possible and light-weight as a result of low power consumption, while assuring high-quality voice production.

This object is achieved with a speech aid of the above-described, known type having a lower output stage for powering an electromechanical vibration transducer. The electromechanical vibration transducer is controlled by an electronic switch. The electronic switch is controlled by a basic pulse signal and adjustment pulses from at least one pulse generator. The adjustment pulses switch off the electronic switch with at least temporal priority over the basic pulse frequency. This assures that all the power which flows from the battery into the power output stage is supplied to the electromechanical transducer so, that no energy is converted into unnecessary heat. The fact that the electronic switch is switched off with temporal priority over the basic signal assures that the basic signal which provides the actual voice-sound producing frequency, is not disturbed.

In a preferred embodiment the controlling pulse generator receives has a basic frequency which is above the upper limit frequency of the electromechanical transducer and produces a basic rectangular signal, the pulse generator being connected to an adjustment member in such a way that the duty cycle of the pulse is determined by the adjustment member. In this preferred embodiment, the basic frequency adjustment is therefore interrupted by a high frequency so that—following low-pass filtering by the transducer—the power but not the frequency of the signal is modified.

In a further preferred embodiment the controlling pulse generator is formed as a univibrator, i.e. as a timing member triggered by the basic signal and connected to an adjustment member in such a way that its time constant is determined by the adjustment member. In this way a specific coherent time area is faded out in each oscillation of the basic signal as a result of which the frequency of the basic signal is maintained and the power of the signal may be modified.

In order to make the speech sound less monotonous, it is possible to increase loudness at the beginning of speech and let it fade away towards the end of a sentence. Skilled users carry this out by pressing and removing the appliance. In order to enable unskilled users to achieve this natural manner of speaking and also to make it easier for skilled users, in a preferred embodiment of the invention the controlling pulse generator is provided with a first auxiliary filter which is coupled to the on/off switch such that on switching on the closing period of the electronic switch rises to the maximum value set by the adjustment member with a predetermined time constant and decreases with a predetermined time constant on switching off. The time constants are preferably approximately 50 ms.

In a further preferred embodiment of the invention, the intonation, as well as the loudness, is controlled during switching on and off. This is achieved by providing the pulse generator for the production of the basic frequency with a further filter which is coupled to the on/off switch such that, on switching on, the frequency of the basic signal increases from a relatively low value to a set pulse generator value with a predetermined time constant and decreases with a predetermined time constant on switching off. The time constants are preferably 50 ms in this case as well.

In order to be able to use the appliance for all voices, the electronic filters, which are conventionally provided and are designed to vary the pulse frequency as a function of time, must be permanently adjusted to specific values. This is achieved in accordance with the invention in that the electronic filters designed to vary the pulse frequency as a function of time comprise removable connections for programming to predetermined values. This ensures high-quality voice production which is adapted to the particular manner of speaking with a minimal expenditure on components —so that the weight of the appliance is kept low.

Voice production may be particularly "clean" if—as in the case of a further preferred embodiment of the invention—the electronic filters comprise a single digital filter with a control logic and an adjustable pulse generator. In this respect the pulse generator for the production of the basic signal is formed as a digitally controlled oscillator. The digital filter preferably operates according to the z-transformation principle. As a result of this digital construction programming is particularly simple and voice production is not dependent on the battery voltage which drops over time, since the operating frequencies of the appliance are essentially independent of voltage. In addition this embodiment ensures a particularly low power consumption as digital components may nowadays be constructed using MOS techniques. The whole appliance may therefore be embodied as an integrated circuit with the result that the weight of the appliance may be considerably reduced.

BRIEF DESCRIPTION OF THE DRAWINGS

FIG. 2 shows a first embodiment of the output stage of FIG. 1;

FIG. 4 shows an output stage of FIG. 2 with loudness control during switching on and off;

DETAILED DESCRIPTION OF THE PREFERRED EMBODIMENTS

Figure 1:
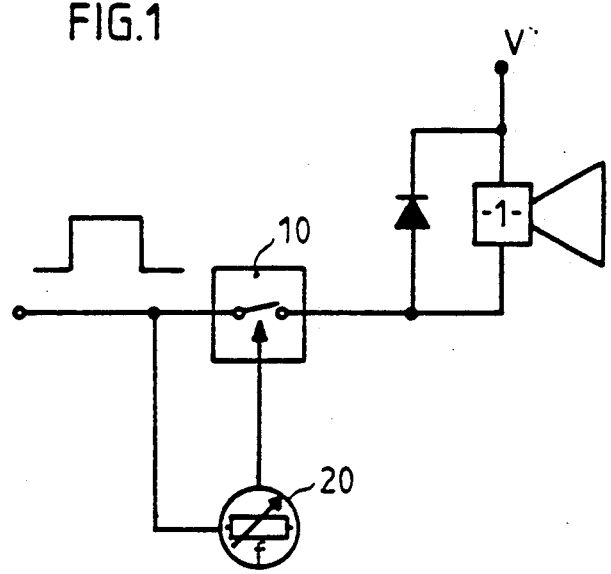
FIG. 1 shows the basic construction of an output stage of the invention.

As shown in FIG. 1, the basic signal comprises a substantially rectangular signal having a frequency in the human voice range which increases from 0 V to a voltage corresponding substantially to the battery voltage and falls away again after a predetermined period. This signal is supplied to the input of the electronic switch 10 which is controlled by a pulse generator 20. In order to make control possible in such a way that the pulse generator 20 can only switch the electronic switch off and not on, the basic signal is supplied to the pulse generator 20 with the basic frequency, which generator then switches the appliance off giving priority to the basic signal.

The signal is supplied from the electronic switch 10 to a terminal of the electromechanical transducer 1 which is preferably embodied as a magnetic system. The other terminal of the transformer 1 is connected to the current source. A protective diode is connected across the terminals.

A preferred embodiment shown in FIG. 2 will now be described in detail.

In this circuit the signal is supplied with the basic frequency to a first input of a NAND-gate 23'. The output of the NAND-gate 23' is connected in parallel to two inputs of a further NAND-gate 23". The output of the NAND-gate 23" is supplied on one hand to the gate connection of a field effect transistor 10 (VMOSFET) and, on the other hand, via a capacitor Cf to the second input of the first NAND-gate 23'. The cathodes and anodes of two diodes D1 and D2 are located on this second input of the first NAND-gate 23'; the anodes and cathodes are respectively connected to an end of a potentiometer 22 via resistances R1 and R2. The centre tapping of the potentiometer lies on the output of the first NAND-gate 23'.

In addition, the electronic switch 10 has one terminal connected to earth and the other terminal connected to the first terminal of the electromechanical transducer 1, which has its second terminal connected to the positive supply potential. The transducer 1 is also bridged by a diode in a known manner.

The mode of operation of the circuit of FIG. 2 will now be described in detail. As soon as the input signal at the first input of the first NAND-gate 23' increases to a positive level, the output of this NAND-gate falls to 0 V, provided that the second input of the NAND-gate 23' is at "1". Since the output of the first NAND-gate 23' decreases to "0", the output of the second NAND-gate 23" increases to "1" as a result of which the transistor 10 is driven. As a result of the increase in the output of the second NAND-gate 23" the first pole of the capacitor Cf is raised to a high potential so that a current flows through the potentiometer 22, the resistor R1 and the diode D1. The capacitor Cf is therefore discharged. As soon as the latter has been charged to the threshold value of the first NAND-gate 23', the output of this gate increases to "1", the second NAND-gate 23" is closed (the transistor 10 is cut off) and the first pole of the capacitor Cf drops to a low potential. The capacitor is thereby charged via the potentiometer 22, the resistor R2 and the diode D2 until its potential again exceeds the threshold value of the first NAND-gate 23' whose output again drops to "0". The process is then repeated. It is evident from the above that the period of time during which the transistor 10 is driven is determined by the potentiometer 22, the resistor R1 and the diode D1 and that the switching off time of the transistor 10 is determined by the other portion of the potentiometer 22, the resistor R2 and the diode D2. By adjustment of the potentiometer 22 it is not therefore the frequency which is determined but the pulse ratio of this pulse generator.

When the first input of the first NAND-gate 23' is at "0", its output is at "1" irrespective of the potential at its second input and consequently the output of the second NAND-gate 23" is at "0" so that the transistor remains cut off. This ensures the above-mentioned "priority control".

Figure 3:
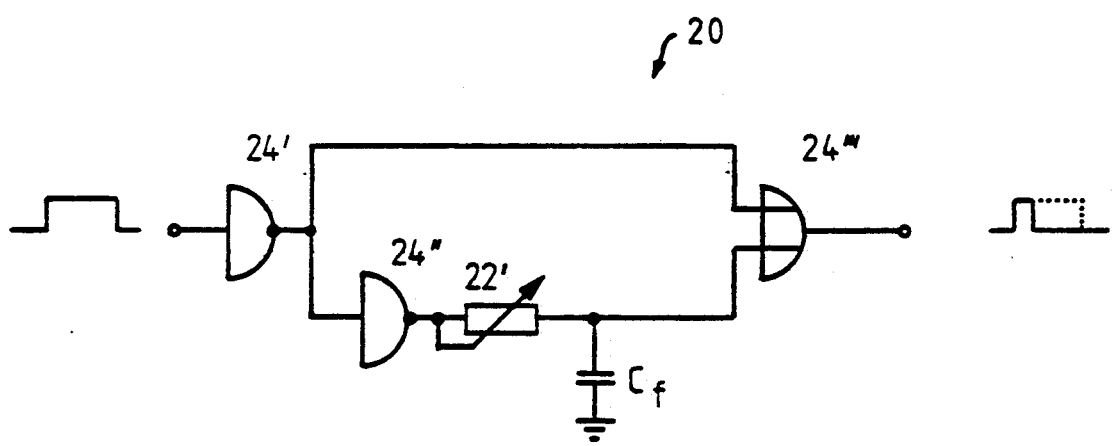
FIG. 3 shows a further embodiment of the output stage of FIG. 1.

A further preferred embodiment of the invention will now be described with reference to FIG. 3, which shows a pulse generator 20 comprising two NAND-gates 24', 24", an OR-gate 24''', a capacitor Cf and an adjustable resistor 22'. This component which is known per se represents ar univibrator which is triggered by a flank increasing from "0" to "1" and remains switched for a predetermined period of time which is determined by the adjustable resistor 22' and the capacitor Cf. In this respect it is also ensured with this circuit that the output "1" may only be present at the OR-gate 24''' if there is a "1" at the input of the first NAND-gate 24'. It is obviously possible to use conventional univibrators in integrated circuits instead of this circuit which is known per se. The output of the OR-gate 24''' is connected to the gate input of the field effect transistor 10 (not shown in this case).

A preferred embodiment of the circuit of FIG. 2 will now be described with reference to FIG. 4 in which the loudness of the voice reproduction, i.e. the power supplied to the transducer 1, increases on switching on with a predetermined time constant and falls away again on switching off with a predetermined time constant. In this embodiment of the invention one pole of an on/off switch S is connected to the positive supply voltage and its other pole is connected to the first terminal of a capacitor C. The other terminal of the capacitor C is connected to an earthed resistor R and to one pole of a light-emitting diode whose other pole is earthed. The light-emitting diode is optically coupled to the gate of a field effect transistor T both of whose other terminals bridge the resistor R1. The field effect transistor T operates in this case as a controllable resistor whose resistance value is dependent on the light current emerging from the light-emitting diode.

The mode of operation of the circuit shown in FIG. 4 is as follows:

When the user presses the on/off switch S, the capacitor C is connected to the supply voltage. It is charged via the resistor R1 and the light-emitting diode by means of the time constant determined by its capacitance and the current which is flowing. During this charging period, the photoelectric current emitted by the light-emitting diode drops and slowly cuts the field effect transistor off again so that its resistance value increases. Since the field effect transistor T is connected in parallel with the resistor R1 which jointly determines the drive time of the transistor 20, the loudness set by the potentiometer 22 increases gradually after switching on to its predetermined value.

On switching off the loudness gradually decreases. Care must be taken to ensure that the field effect transistor has, when the light-emitting diode is not emitting any light current, a resistance value which is high enough to ensure that the duration of connection of the transistor 10 is only determined by R1.

Control may be carried out by a generator using analog or digital techniques.

The circuit of the speech aid upstream of the output stage will now be described with reference to FIG. 5.

As this drawing shows, the circuit comprises a voltage-controlled oscillator 12 (VCO) whose output represents the signal with the basic frequency. The control input of the VCO 12 is connected to four summing resistors R whose other ends are connected to the outputs of four components E, D, I and M. The output frequency of the VCO 12 is therefore produced as a function of the sum of the output voltages of the above components. The components E, D, I and M are described in detail below.

The component E comprises a resistance network RF with several resistors connected in series whose points of connection are located on respective sockets RF1-RFn. The network is connected at one end to the supply voltage and at its other end to a ballast resistor and simultaneously to one of the summing resistors R. The output voltage of the component E is modified according to the way in which the individual resistors in the network RF are connected across the terminals RF1-RFn via short-circuiting bridges. This output voltage determines the "end frequency" as will be described in detail below.

The component D comprises two similar resistance networks RS with connections RS1-RSn and RD with connections RD1-RDn. The first resistance network RS is connected at one end to the supply voltage and at its other end via a ballast resistor to the first pole of a switch S1. The first pole of the resistance network RD is connected to earth and its other pole to the second contact of the switch S1. The summing pole of the switch S1 is connected to an earthed capacitor CD and to a summing resistance R.

Figure 5:
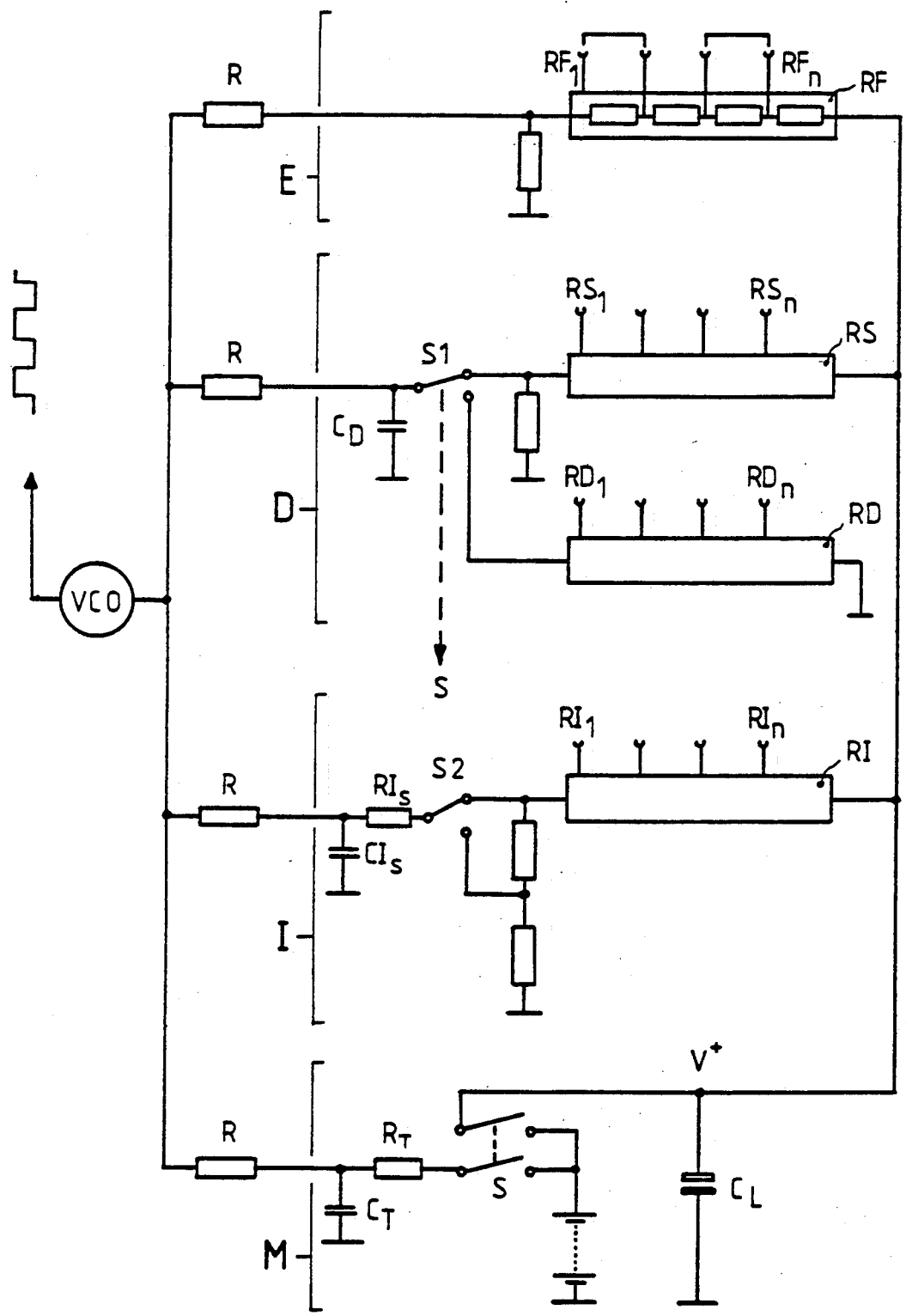
FIG. 5 shows a basic circuit for tone production with analog components.

The component D operates as follows:

If the switch S1 is in the position shown in FIG. 5, the capacitor CD is charged via the resistance network RS to the voltage value determined by the ballast resistor at the output of the resistance network RS, which value is then added to the input of the VCO 12. If the switch is moved into its second position (not shown) the capacitor CD is completely discharged via the network RD.

As the outputs of the components E and D are added, the total voltage from the components E and D never falls below the value determined by the component E.

The component I will now be described. The component I comprises a resistance network RI with connections RI1-RIn (as described above) and has one end connected to the positive supply voltage and the other end connected to a series connection of two resistors which is again earthed so that a series connection of three resistance components is produced. The central resistance component has both terminals connected to two terminals of a switch S2 whose summing terminal is connected via a resistor RIS and an earthed capacitor CIS to a summing resistor.

The component operates as follows: if the switch S2 is in the position shown in FIG. 5, the output voltage of the component I is determined by the voltage drop at the resistance network RI. If the switch S2 is moved into its second position, the voltage drops with the time constant determined by the resistor RIS and the capacitor CS to a relatively low voltage which is determined by the voltage drop via the resistance network RI and the resistor connected downstream.

The mode of operation of the component M will now be described. If the switch S is in the position shown in FIG. 5, the battery is uncoupled and the supply voltage V+ is 0. If the switch S is moved into its second position, the charging capacitor CL is rapidly charged (as a result of the low battery impedance), while a capacitor CT connected to earth is only gradually charged via a resistor RT. The voltage at the capacitor CT is supplied to a summing resistor R.

The overall mode of operation of the circuit is as follows: the switch S is mechanically connected to the switch S1 in such a way that in the rest condition they are in the position shown in FIG. 5. If the user presses the switch S/S1 the VCO control voltage increases from a value determined by the total output voltage of the components E, D and I to the total sum value. A short time constant is selected in this respect for the component M, preferably 50 ms. After this rapid increase in the input voltage for the VCO 12 the latter then falls again slowly, as a function of the time constants from the capacitor CD and the resistance network RD, to an end value which is substantially the sum of the output voltages from the components E, I and M. This slow decrease in the total voltage causes a slow drop in the output frequency of the VCO 12 so that the normal fall in the level of the voice during a sentence heard in natural speech is ensured.

If the switch S2 of the component I is pressed down from its rest position to the position shown in FIG. 5, it causes a rise in the "voice frequency" and if it is released it causes a drop in the voice frequency, the rise and fall times being determined by the timing member RIs, CIs (the "raised" position is therefore shown in FIG. 5). This "intonation jump" leads to comparatively natural speech reproduction.

Since the resistance networks RF, RS, RD and RI are respectively provided with tapping points which may be short-circuited via simple bridges it is possible to programme the normal rise and fall during speaking as well as beginning and end positions and an intonation jump in the way required by the language of the user. As these values differ greatly from language to language, it is possible by means of the embodiment of the speech aid of the invention to ensure optimum "programmability" with very little expenditure on components.

A further preferred embodiment of the invention, embodied using digital techniques, will now be described with reference to FIG. 6. The circuit of FIG. 6 comprises a digital oscillator 40 which substantially comprises an oscillator which may be regulated via the connections RP1 and RP2, which oscillator pulses a synchronous counter. The parallel outputs of the synchronous counter are supplied to a comparator which receives its reference values via a latch. When the values from the synchronous counter and the latch are in agreement, an output signal is supplied to the output AU. An output stage as shown in FIGS. 1 to 4 can be coupled to the output AU.

The latch receives its input values from a digital filter 60 which carries out a z-transformation. The coefficients of the z-transformation are in this respect determined by a control logic 64 which comprises programming connections DEC, M1 and M2. The pulse rate of the filter 60 is determined by a second oscillator which comprises programming connections RT1 and RT2.

Figure 6:
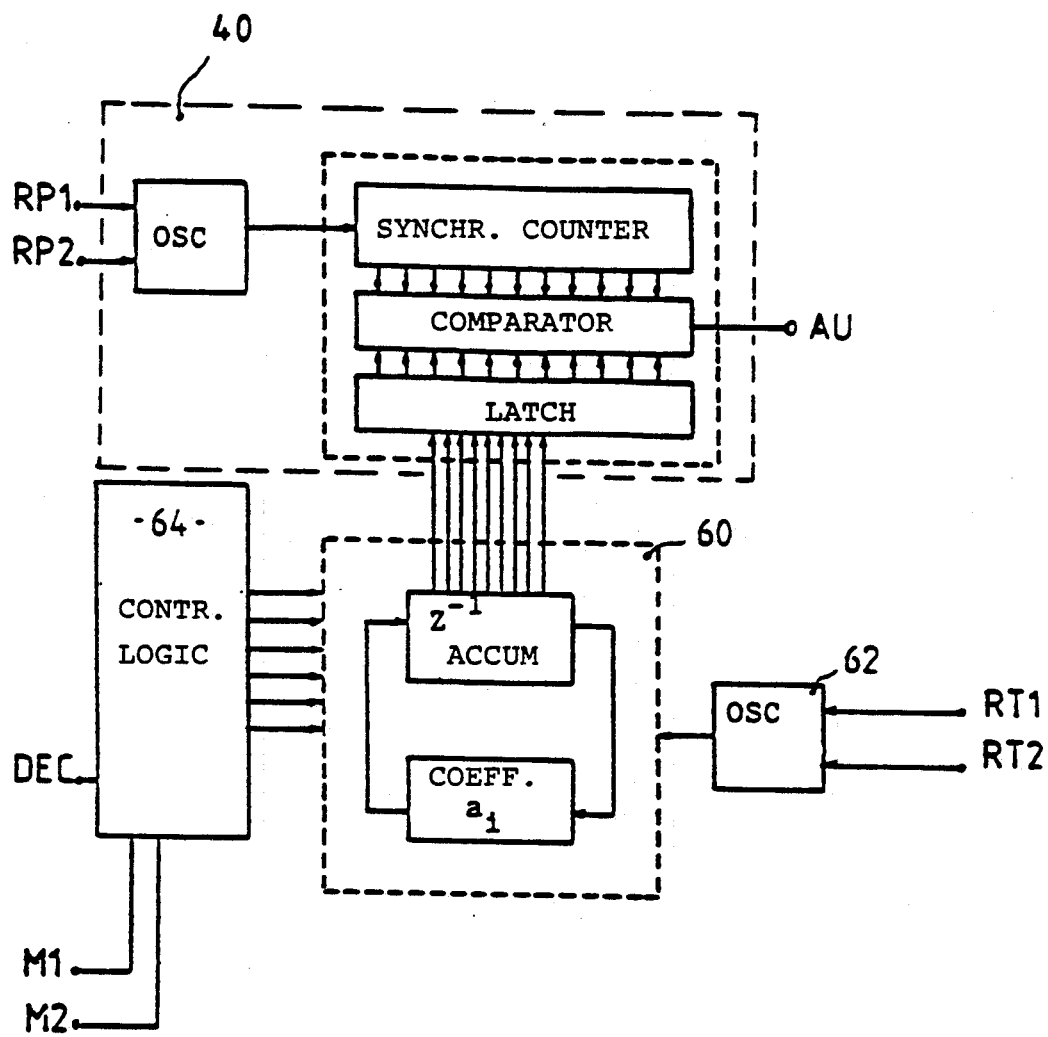
FIG. 6 shows a block diagram of the digital embodiment of the invention.

The mode of operation of the circuit shown in FIG. 6 is as follows: the basic frequency is determined in the pulse generator 40 by the first oscillator. The basic frequency is modified as a function of the values which are supplied from the digital filter 60 via the latch to the comparator. Since the pulse frequency of the digital filter 60 is determined via the programming inputs RT1 and RT2 of the oscillator 62 and the coefficients of the z-transformation are set via the control logic 64 by means of the values at the control inputs DEC, M1 and M2, any frequency behaviour may be programmed in advance. The on/off and intonation switches described in further detail above are obviously used in this respect and are coupled in the manner known to persons skilled in the art. The adjustment of the appliance to the language of the user therefore takes place via the programming inputs RP1, RP2; RT1, RT2 and M1, M2, DEC.

As mentioned above, use may be advantageously made of the output stage (to be coupled to the output AU) described with reference to FIGS. 1 to 4, although a conventional output stage could of course also be used.

It will be understood that the specification and examples are illustrative but not limitative of the present invention and that other embodiments within the spirit and scope of the invention will suggest themselves to those skilled in the art.

What is claimed is:

1. A speech aid to be used by post-laryngectomy patients, comprising:
   (a) an electromechanical transducer responsive to electrical signals having frequencies in the human voice range producing human voice sounds, and non-responsive to electrical signals having frequencies above the human voice range;
   (b) means for generating a basic rectangular pulse signal having a first fundamental frequency in the human voice range;
   (c) means for chopping said basic signal to produce an adjusted basic signal, wherein each rectangular pulse of said basic signal includes a plurality of rectangular pulses having a second fundamental frequency above the human voice range and having a prescribed pulse ratio, said chopping means including means for varying said pulse ratio, said varying means including a potentiometer to permit manual adjustment of said pulse ratio;
   (d) power switch means, electrically coupled to said transducer, for opening and closing an electrical circuit path through said transducer in response to said adjusted basic signal;
   whereby said transducer is driven at said first frequency with the power determined by the pulse ratio of the pulses at said second frequency.

2. A speech aid to be used by post-laryngectomy patients, comprising:
   (a) an electromechanical transducer responsive to electrical signals having frequencies in the human voice range producing human voice sounds, and non-responsive to electrical signals having frequencies above the human voice range;
   (b) means for generating a basic rectangular pulse signal having a first fundamental frequency in the human voice range;
   (c) means for chopping said basic signal to produce an adjusted basic signal, wherein each rectangular pulse of said basic signal includes a plurality of rectangular pulses having a second fundamental frequency above the human voice range and having a prescribed pulse ratio, said chopping means including a NAND gate having first and second inputs and an output, said NAND gate being connected to receive said basic signal at said first input; an inverting gate having an input connected to said output of said NAND gate and an output coupled to a power switch means; a capacitor having two terminals, one terminal being connected to said output of said inverting gate and the other terminal being connected to said second terminal of said NAND gate; first and second resistance paths each connected between said output of said NAND gate and said other terminal of said capacitor, each resistance path having a diode arranged therein, said diodes being oriented to conduct in opposite directions;
   (d) said power switch means being electrically coupled to said transducer for opening and closing an electrical circuit path through said transducer in response to said adjusted basic signal;
   whereby said transducer is driven at said first frequency with the power determined by the pulse ratio of the pulses at said second frequency.

3. The speech aid defined in claim 2, wherein said first and second resistance paths each include a potentiometer.

4. The speech aid defined in claim 3, wherein said potentiometer has a conductance path therethrough between first and second terminals and an adjustable tap member arranged to contact a prescribed point along said conductance path, said tap member being connected to said output of said NAND gate and said first and second terminals being coupled to said diodes in said first and second resistance paths, respectively.

5. The speech aid defined in claim 2, wherein at least one resistance path includes a optically responsive device, connected across at least a portion of the resistance of said path, for reducing said resistance in response to a light signal; and a light transmitting device, optically coupled to said optically responsive device, for selectively transmitting light to said optically responsive device.

6. The speech aid defined in claim 5, wherein said light transmitting device includes a manually adjustable mechanical switch for switching said light transmitting device on and off.

7. The speech aid defined in claim 6, wherein said light transmitting device further includes a light transmitting element and an electrical filter, connected to said light transmitting element, for slowly increasing and slowly decreasing the current applied to said light transmitting element, respectively, when said mechanical switch is turned on and off.

* * * * *

UNITED STATES PATENT AND TRADEMARK OFFICE
CERTIFICATE OF CORRECTION

PATENT NO. : 4,993,071

DATED : February 12, 1991

INVENTOR(S) : Peter Griebel

It is certified that error appears in the above-identified patent and that said Letters Patent is hereby corrected as shown below:

Column 3, line 57, after "potential" insert $--V^+--$.

Signed and Sealed this

Sixth Day of July, 1993

Attest:

MICHAEL K. KIRK

Attesting Officer — Acting Commissioner of Patents and Trademarks